US00PP08630P

United States Patent [19]

Zary

[11] Patent Number: Plant 8,630

[45] Date of Patent: Mar. 8, 1994

[54] HYBRID TEA ROSE PLANT NAMED 'JACEM'

[75] Inventor: Keith W. Zary, Thousand Oaks, Calif.

[73] Assignee: Bear Creek Gardens, Inc., Medford, Oreg.

[21] Appl. No.: 990,741

[22] Filed: Dec. 15, 1992

[51] Int. Cl.[5] ..... A01H 5/00

[52] U.S. Cl. ..... Plt./18

[58] Field of Search ..... Plt. 18

*Primary Examiner*—Howard J. Locker

*Attorney, Agent, or Firm*—Klarquist, Sparkman, Campbell, Leigh and Whinston

[57] ABSTRACT

Hybrid tea rose plant capable of high production of long-stemmed large blooms of light pink, having strong fragrance and long vase life.

1 Drawing Sheet

1

The present invention relates to a new and distinct variety of rose plant of the Hybrid tea class which was originated by me by crossing the variety INTERval, U.S. Plant Pat. No. 5,648, with the variety KORampa, U.S. Plant Pat. No. 5,411.

The primary objective of this breeding was to produce a new rose variety having the fragrance and flower size of the female parent INTERval combined with the high production and lack of thorns of the male parent KORampa. The objective was substantially achieved along with other desirable improvements as evidenced by the following unique combination of characteristics which are outstanding in the new variety and which distinguish it from its parents, as well as from all other varieties of which I am aware:

1. Strong, heavy fragrance;
2. Large, well-shaped hybrid tea flowers;
3. High production (30–35 stems per plant) of long-stemmed flowers;
4. Good vase life;
5. Few thorns.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed Parent.*—INTERval.

*Pollen Parent.*—KORampa.

Classification:

*Botanical.*—Rosa hybrida.

*Commercial.*—Hybrid tea.

2

FLOWER

Observations made from specimens grown in a greenhouse environment in Somis, Calif., from January to June, 1992.

Blooming Habit: Recurrent.

Bud:

*Size.*—1¼" when the petals start to unfurl.

*Form.*—Long, pointed ovoid.

*Color.*—When sepals first divide, bud color is Red Group 36D, becoming more intense (Red Group 36A) on the tip of the bud. When half blown, the upper and lower sides of the petals are Red Group 36D.

*Sepals.*—Color: Green Group 138C. Surface texture: Covered with fine hairs. There are three normally appendaged sepals. There are two unappendaged sepals with hairy edges.

*Receptacle.*—Color: Green Group 137C. Shape: Funnel. Size: Small. Surface: Smooth.

*Peduncle.*—Length: Medium. Surface: Smooth. Color: Medium green. Strength: Stiff, erect.

Bloom:

*Size.*—Large. Average open size is 4" to 4½".

*Borne.*—Singly.

*Stems.*—Long, strong, 22 to 26".

*Form.*—When first open: High centered. Permanence: Retains its form to the end, outer petals curl back.

*Petalage.*—Number of petals under normal conditions: 25 to 30.

*Color.*—The upper and reverse sides of the petals are Red Group 36D. The bases of the petals have a yellow half moon at the point of attachment. The major color on the upper side is Red Group 36D.

*Variegations.*—Occasional green streak on the guard petals.

*Discoloration.*—The general tonality at the end of the first day: None. At the end of the third day: None.

*Fragrance.*—Strong.

Petals:

*Texture.*—Thick.

*Shape.*—Round.

*Form.*—Tips slightly recurved, moderately quilled.

*Arrangement.*—Imbricated, with few petaloids in the center.

*Persistence.*—Hang on and dry.

*Lastingness.*—On the plant: Long, 7 days. As a cut flower: Long, 9 days.

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Red.

Form: Bush.

Growth: Very vigorous, upright and branching.

Foliage: Number of leaflets on normal mid-stem leaves: 5.

*Size.*—Medium, 5½"×4".

*Quantity.*—Abundant.

*Color.*—New foliage: Deep maroon. Old foliage: Dark green.

Leaflets:

*Shape.*—Pointed oval.

*Texture.*—Upper side: Leathery, semi-glossy.

*Edge.*—Serrated.

*Serrations.*—Single.

*Petiole rachis.*—Color: Reddish.

*Petiole underside.*—Rough with prickles.

*Stipules.*—Medium, serrated.

*Disease resistance.*—Resistant to mildew under normal growing conditions in a greenhouse environment at Somis, Calif.

Wood:

*New wood.*—Color: Reddish. Bark: Smooth.

*Old wood.*—Color: Green. Bark: Smooth.

Prickles:

*Quantity.*—On main canes from base: Few. On laterals from main canes: Few.

*Form.*—Medium, hooked slightly downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its high production of long-stemmed cut-flower blooms, strong fragrance, few thorns, long vase life and its large, attractive, light pink flowers.

* * * * *

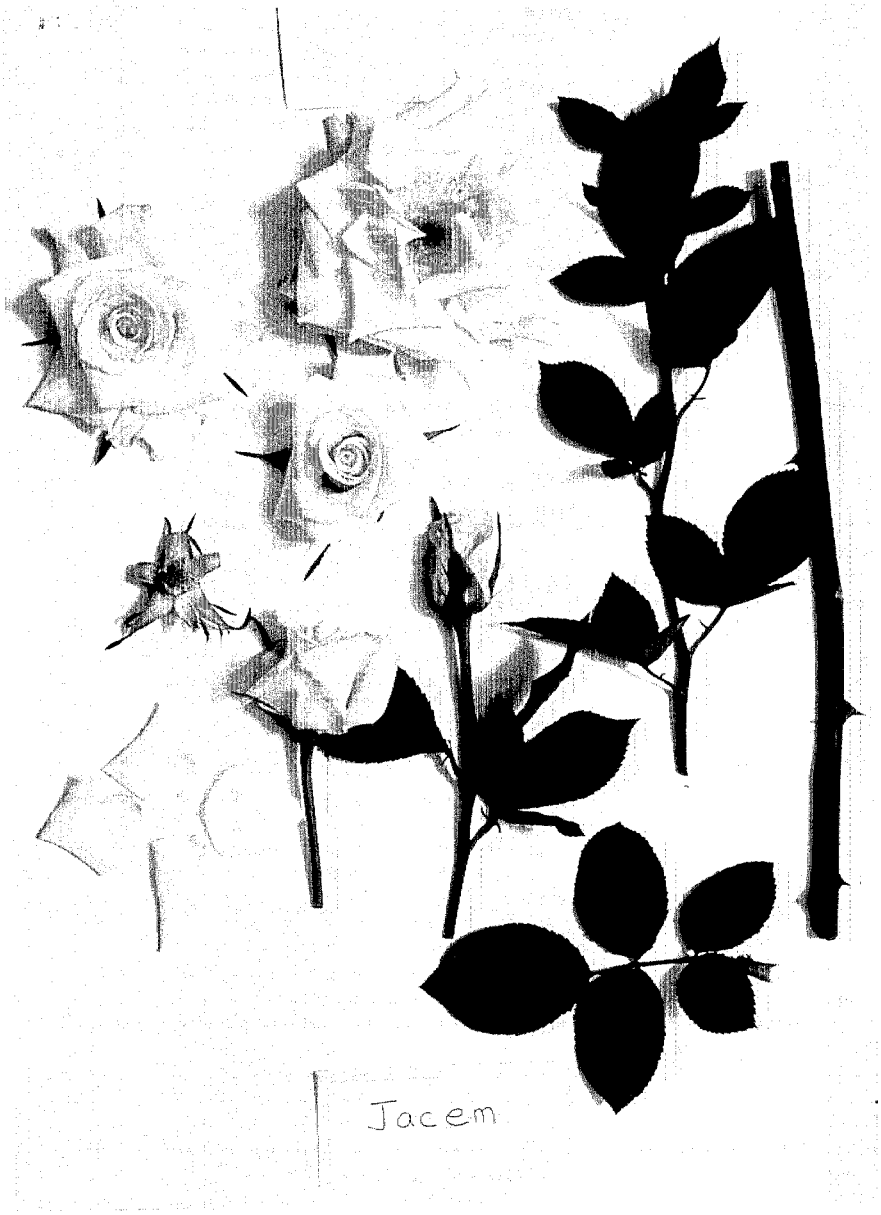
Jacem